(12) United States Patent
Albert

(10) Patent No.: US 10,493,302 B2
(45) Date of Patent: *Dec. 3, 2019

(54) COMPOSITIONS FOR HUMAN DENTAL CARE

(71) Applicant: Karen L. Albert, Malibu, CA (US)

(72) Inventor: Karen L. Albert, Malibu, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/725,149

(22) Filed: Oct. 4, 2017

(65) Prior Publication Data

US 2018/0028843 A1 Feb. 1, 2018

Related U.S. Application Data

(63) Continuation of application No. 12/384,981, filed on Apr. 10, 2009, now abandoned.

(60) Provisional application No. 61/123,615, filed on Apr. 10, 2008.

(51) Int. Cl.
| | |
|---|---|
| *A61Q 11/02* | (2006.01) |
| *A61Q 11/00* | (2006.01) |
| *A61K 8/66* | (2006.01) |
| *A61K 8/97* | (2017.01) |
| *A61Q 17/00* | (2006.01) |

(52) U.S. Cl.
CPC ............... *A61Q 11/00* (2013.01); *A61K 8/66* (2013.01); *A61K 8/97* (2013.01); *A61Q 17/005* (2013.01)

(58) Field of Classification Search
CPC ....... A61Q 11/02; A61Q 17/005; A61Q 11/00
See application file for complete search history.

(56) References Cited

U.S. PATENT DOCUMENTS

| | | | |
|---|---|---|---|
| 4,508,713 A | 4/1985 | Stroz et al. | |
| 6,503,483 B2 | 1/2003 | Shuch et al. | |
| 2001/0036488 A1 | 11/2001 | Hayashi et al. | |
| 2003/0003059 A1 | 1/2003 | Dana | |
| 2005/0158252 A1 | 7/2005 | Romanowski et al. | |
| 2005/0208194 A1 | 9/2005 | Valovic et al. | |
| 2006/0140883 A1 | 6/2006 | Trivedi et al. | |
| 2006/0140884 A1 | 6/2006 | Worrell et al. | |
| 2006/0175579 A1 | 8/2006 | Nunez et al. | |
| 2006/0269438 A1 | 11/2006 | Lagunas-Solar et al. | |
| 2008/0031831 A1 | 2/2008 | Laali | |
| 2008/0050500 A1 | 2/2008 | Muranishi | |

OTHER PUBLICATIONS

Reader's Digest: http://www.rd.com/health/bahish-bad-breath; Jun. 15, 2011.
Yilmaz, et al., (J. Agric. Food Chem. 2004, 52, 255-260).
Chatterjee, et al., Appl. Environ. Microbiol., Apr. 2006, vol. 72, No. 4, pp. 2627-2636.
Wikipedia (http://en.wikipedia.org/wiki/Growth_medium.) (Accessed Oct. 24, 2013).
United States Department of Agriculture. Agricultural Research Service. National Nutrient Database for Standard Reference Release 28. Full Report (All Nutrients): 09050, Blueberries, raw. Accessed Oct. 20, 2015.
United States Department of Agriculture. Agricultural Research Service. National Nutrient Database for Standard Reference Release 28. Basic Report: 09286, Pomegranates, raw. Accessed Oct. 20, 2015.

*Primary Examiner* — Rachael E Bredefeld
*Assistant Examiner* — Chris E Simmons
(74) *Attorney, Agent, or Firm* — Morriss O'Bryant Compagni Cannon, PLLC

(57) ABSTRACT

Compositions of the invention are water-based formulas that contain natural ingredients which aid in reduction of bacteria in the mouth, thereby reducing plaque and the production of tartar, and in one aspect of the invention are formulated as potable dental water that may be consumed in place of regular consumption of other forms of water or liquid, and in another aspect of the invention are formulated as dentifrices, such as toothpaste.

4 Claims, No Drawings

COMPOSITIONS FOR HUMAN DENTAL CARE

CROSS-REFERENCE TO RELATED APPLICATION

This application is a non-provisional application claiming priority to provisional patent application Ser. No. 61/123,615 filed Apr. 10, 2008.

BACKGROUND OF THE INVENTION

Field of the Invention

This invention relates to healthcare products for humans, and specifically relates to compositions for the benefit of dental care in humans.

Description of Related Art

Dental health care is well-known to be critical to the overall health of humans. Good dental health plays an important role in maintaining not only the cosmetic look of a person's mouth and smile, but is important in maintaining the level of health in other systems of the human body.

It is known that both the deciduous and permanent teeth of humans deteriorate over time and are subject to numerous dental diseases. Dental caries, or cavities, is the most common aspect of tooth deterioration and is caused by bacterial processes fueled by the presence of fermentable carbohydrates, or sugars. Plaque build-up on teeth, another critical feature of tooth decay, leads to inflammation, gum deterioration and weakening of the teeth such that tooth loss may become inevitable.

Gum disease, painful teeth and other dental disease conditions can lead to significant discomfort, loss of appetite and general ill health. It has recently been shown that poor dental health can play a significant role in adversely affecting the heart, kidneys and other organ systems. Poor dental health is known to spread bacteria to other parts of the body, thereby leading to deleterious health conditions in other areas of the body. Most recently, poor dental health has been directly linked with an increased chance of heart attack.

Despite the well-known benefits of maintaining good dental health, many people do not practice adequate or regular dental care. Surprisingly, many people fail to floss their teeth, use mouthwash or brush on a regular basis. It has been shown, more commonly, that while people brush their teeth at least twice a day, the time spent on the brushing process is measurable in matters of seconds, which is seriously inadequate. Consequently, the beneficial effects of brushing are not achieved.

At the same time, there has been an increased interest in avoiding harsh and/or unnatural chemicals and ingredients in all consumer products. This has lead to an increased interest in consumer products that contain or are based on natural ingredients. Along with the increased interest in natural products has come a desire to pursue more healthy habits to increase good health and extend longevity. One of these interests has been an increased awareness for the need to consume eight glasses of water each day to aid and promote proper hydration in the body.

Therefore, in the interest of promoting healthy dental habits while employing natural ingredients, it would be beneficial to provide means for facilitating beneficial dental healthcare using natural ingredients, while also, in one aspect, promoting healthcare through the consumption of water for proper hydration.

BRIEF SUMMARY OF THE INVENTION

In accordance with the present invention, comestible, non-medicated compositions are provided which prevent, treat and/or stop the progression of dental disease, and improve the dental health of humans. A composition, in one aspect of the invention, is a water-based product that can be formulated for consumption as a cost-effective and easily-administered means of facilitating dental healthcare while promoting proper daily hydration. In another aspect of the invention, compositions are formulated as non-liquid dentifrices that contain natural ingredients.

In one aspect of the invention, a water-based composition is formulated with natural ingredients that promote a healthy environment within the mouth to prevent the formation of caries and the build-up of plaque. Among the natural ingredients of the composition are active ingredients that reduce bacteria in the mouth and anti-bacterial agents that also reduce and/or prevent the proliferation of bacteria in the mouth. Other ingredients may include agents that facilitate an immune response to bacteria, such as antioxidants.

The composition may also include vitamins, flavoring agents and breath-freshening agents to promote clean breath. Also included in the composition may be agents that are effective to coat the mouth with the composition, or promote adherence of the composition to the teeth to maximize the bacteria-reducing and breath-freshening benefits of the composition.

The invention may, in one aspect, be formulated as a concentrate that can be added to a selected amount of water to produce a potable water product that can be consumed daily. In another aspect of the invention, a potable water product is disclosed which can be consumed as a replacement for the consumption of other forms of liquid including tap water, bottled water, spring water, soda water, soda, coffee, tea or specially formulated beverages, such as sports drinks and the like. Because the dental water of the invention can be used to replace other forms of water, it can be consumed either hot or cold, and can be used in virtually any form of cooking. Additionally, the dental water of the present invention can also be mixed with or formulated with other healthful ingredients, such as fiber, to provide not only dental care and normally daily hydration, but a daily dose of fiber to promote healthy gastrointestinal function.

While the potable dental water of the present invention can be formulated with little or no flavor characteristic, the potable water can also be formulated with flavorings to enhance the drinkability of the product. Flavoring the potable dental water may render the water particularly more pleasing to children so that the dental health of children can be enhanced by consumption of the invention.

The potable dental water of the present invention may also be particularly useful to serve the dental needs of special-needs individuals, such as invalids of other people who are unable to practice conventional daily dental hygiene. Also, the potable dental water may be particularly useful for emergency use, such as in disasters when victims of natural disasters are unable to practice conventional daily dental hygiene, but can be provided drinking water through relief aid sources, such as FEMA, to remain hydrated while still practicing a form of dental hygiene.

In another aspect of the invention, compositions are formulated as toothpaste or other dentifrices for use in brushing the teeth. The dentifrice compositions are water-based and include natural ingredients that reduce bacteria and prevent proliferation of bacteria in the mouth. The dentifrice compositions are formulated for everyday use by both adults and children as part of a conventional dental hygiene regimen.

DETAILED DESCRIPTION OF THE INVENTION

In one aspect of the invention, the composition of the invention is a water-based formula that contains natural ingredients which aid in reduction of bacteria in the mouth, thereby reducing plaque and the production of tartar. The composition contains natural ingredients that freshen the breath and, in one respect, act like a mouthwash that helps prevent the accumulation of bacteria. The composition or formulation also coats the buccal (mouth) cavity to provide continuous protection against the accumulation of bacteria. The composition includes natural ingredients that provide various benefits toward reducing bacteria and freshening the breath.

The composition includes at least two active ingredients which mediate the reduction of bacteria in the mouth. Natural enzymes, such as papain or bromelain or other similar enzymes, or combinations thereof, are included in the composition to effectively reduce the build-up of proteins in the mouth and thereby reduce bacterial proliferation. The composition further includes one or more antibacterial agents that effectively reduce bacterial proliferation. Such agents may particularly include zinc gluconate and spice extracts, such as cinnamon, clove and parsley seed oil and combinations of those and other spice extracts.

The composition also includes natural antioxidants that increase or facilitate an immune response to bacteria. Any number or type of antioxidants from natural sources, preferably plant sources, can be used in the composition. Such antioxidants may include, for example, grape skin extract, grape seed extract, blueberry and/or pomegranate extracts and other anthocyanins or similar antioxidants derived from edible and natural sources. Blueberry and pomegranate extracts that are particularly preferred for use are those that are produced from freeze dried juices using low temperature and vacuum extraction to preserve the vitamins, minerals and antioxidants found in the original plant source.

The composition may also include vitamins which are also antioxidants and which help increase the immune response to bacteria. For example, the composition may include vitamins B and C, as well as other vitamins. It has been shown in development of the compositions of the invention that the antioxidant effects of anthocyanins and vitamins have a greater effect in combination than such antioxidants alone, thereby providing a beneficial cumulative effect.

The composition may include chlorophyll as a natural substance for freshening the breath. Flavoring agents may be added as well to not only increase the palatability of the composition, but to enhance the ability of the composition to produce fresher breath. Flavoring agents may include, by way of example, extracts of clove and/or cinnamon, and citrus flavorings. Any number, type or combination of flavorings is possible.

The composition may also include agents that help coat the mouth with the fluid of the composition or formulation to increase its overall effectiveness. Such agents may include glycerin, which itself has antiseptic properties, and zinc gluconate. The formula may also include a gum or gum extract such as guar or locust bean gum, xanthan gum or carrageenan gum to effect substantial adherence of the product to the teeth.

An exemplar formulation of the water-based composition is as follows:

EXAMPLE 1

| Ingredient | Amount |
| --- | --- |
| Purified Water | 70% to 90% by volume |
| Glycerin | 5.0% to 10.0% by volume |
| Blueberry | 0.1% to 1.0% by volume |
| Yucca Extract | 0.1% to 1.0% by volume |
| Zinc Gluconate | 0.01% to 0.5% by volume |
| Pomegranate | 0.01% to 2.0% by volume |
| Papain | 0.01% to 0.5% by volume |
| Riboflavin | 0.01% to 0.08% by volume |
| Ascorbic acid | 0.01% to 0.1% by volume |
| Clove Extract | 0.01% to 0.5% by volume |
| Cinnamon Extract | 0.01% to 0.5% by volume |
| Parsley seed oil | 0.1% to 0.5% by volume |
| Chlorophyll | 0.1% to 0.5% by volume |
| Xanthan gum | 0.1% to 0.5% by volume |
| Flavoring | 0.1% to 0.5% by volume |

The composition is made by adding the glycerin to approximately three-quarters of the amount of purified water in a stainless steel tank equipped with mixing apparatus. The mixture is stirred until well-blended. The blueberry, Yucca extract, riboflavin, ascorbic acid, zinc gluconate, papain, pomegranate, clove and cinnamon extracts are then added and the mixture is stirred until a homogeneous fluid is achieved. The chlorophyll, xanthan gum and flavoring is then added and the material is stirred until the chlorophyll is uniformly mixed throughout. The balance of purified water is added and mixed until uniformly distributed.

The foregoing composition provides a concentrate from which is prepared a shelf-stable, potable dental water that can be consumed or used as a replacement for other forms of water, such as tap water or bottled water.

The potable dental water is produced as follows:

EXAMPLE 2

To one quart of purified water is added five milliliters (5 ml) of the concentrate composition made in accordance with Example 1. The resulting quart of potable dental water is then placed in appropriate containers containing a desired amount of the composition. The containers may be of any desired volume, including a four ounce portion which may be suitable for providing to children, or from six to twenty-four or more ounces for adult consumption.

A single daily dose of the dental water formulation for children is from about 0.5 liters to about 2.0 liters, depending on the size and age of the child. A recommended single daily dosage of the dental water formulation for adult humans is from between about 200 ml to about 4000 ml, with a minimum recommended daily dose of about 400 ml. The dental water formulation can be consumed in an amount characteristic of the amount of water that is needed to stay hydrated. Therefore, one can consume whatever amount of the composition is required for the consumer's hydration needs, or in a conscientious regimen of eight glasses (8 ounce) per day for an adult. The dental water formulation is not toxic, and it is virtually impossible to consume too much of the dental water in a day.

A daily dosage, or any desired amount, of the dental water formulation can be packaged in any appropriate container, such as a bottle. A single recommended dosage of 400 ml, or several alliquotes, can be contained in a bottle to be consumed as desired. The dental water can also be frozen in the form of ice cubes or popsicles and consumed in such form.

In a particularly suitable packaging arrangement, a desired amount of the composition can be contained in a closed, resealable container, such as a bottle. The container can be sized for retaining any amount of fluid, but, for example, may contain from eight to twenty ounces of the composition in a single bottle. The container may also be filled with the appropriate amount of a single or daily dosage of the composition to facilitate administration of the appropriate amount of fluid for a given day.

In a second aspect of the invention, the composition of the present invention may be formulated as a toothpaste or similar dentifrice. An exemplar formula for toothpaste is as follows:

EXAMPLE 3

| | |
|---|---|
| Water | 10% to 20% by weight |
| Sorbitol | 20% to 30% by weight |
| Sodium bicarbonate or calcium carbonate | 30% to 45% by weight |
| Glycerin | 10% to 20% by weight |
| Potassium sorbate | 0.1% to 0.5% by weight |
| Xanthan gum | 0.1% to 0.5% by weight |
| Flavoring | 0.1% to 0.5% by weight |
| Tetrasodium pyrophosphate | 2% to 6% by weight |
| Chlorophyll | 0.01% to 0.1% by weight |
| Parsley Seed Oil | 0.01% to 0.5% by weight |
| Cinnamon Extract | 0.01% to 0.5% by weight |
| Clove Extract | 0.01% to 0.5% by weight |
| Papain | 0.05% to 0.5% by weight |
| Pomegranate | 0.1% to 1.0% by weight |
| Blueberry | 0.05% to 0.5% by weight |
| Zinc Gluconate | 0.05% to 0.5% by weight |

The toothpaste composition is made by adding the water (preferably purified or "safe" water) to a stainless steel vessel and heating the water to 50° C. The potassium sorbate is added and the fluid mixed until the potassium sorbate is dissolved. The zinc gluconate is then added and the fluid mixed until the zinc gluconate is dissolved. The sorbitol is added and mixed until evenly dispersed, and then the papain, cinnamon and clove are added and the fluid mixed until evenly dispersed. The pomegranate, blueberry, chlorophyll and parsley seed oil are then added and the fluid mixed until all ingredients are dispersed evenly. The bicarbonate or carbonate is added and the material is mixed to maintain the suspension of materials. Tetrasodium pyrophosphate is then added and the material is continuously mixed to maintain suspension. In a separate vessel, the xanthan gum is dispersed in the glycerin and mixed until the gum is evenly dispersed. The xanthan gum mixture is then added to the other materials in the main vessel and mixed until all ingredients are thoroughly dispersed and the composition is thick.

The toothpaste composition may be used in the same manner and with the same frequency as commercial toothpastes, i.e., at least twice a day in accordance with a recommended daily dental regimen. The toothpaste of the present invention may also be used on animals as a part of dental care for pets.

The compositions of the present invention are directed to providing a water-based formula containing natural ingredients for the reduction and prevention of bacterial conditions in the mouth. The main compositions are disclosed herein for use in a potable dental water and dentifrices for cleansing the teeth. Other and related formulations of the basic compositions can be adapted for use in any other aspect of daily dental hygiene, including, for example, mouth rinses and tooth polishing or whitening formulas. Hence, reference herein to specific embodiments or ingredients is by way of example only and not by way of limitation.

What is claimed is:

1. A method for providing a dental care agent to humans comprising administering to a human a potable aqueous composition containing a combination of surfactant agents comprising yucca extract, cinnamon extract and clove extract to provide, in combination, a reduction of plaque on teeth, said aqueous composition further comprising an effective amount of at least one active ingredient for reducing bacterial proliferation in the mouth and at least one adhering agent.

2. The method of claim 1, wherein said dental care agent comprises
the potable aqueous composition containing
an aqueous plaque-reducing composition, wherein the aqueous plaque-reducing composition contains
i) the combination of surfactants, said combination of surfactant agents comprises yucca extract in an amount of between 0.1% to 1.0% by volume of the aqueous plaque-reducing composition, clove extract in an amount of between 0.01% to 0.5% by volume of the aqueous plaque-reducing composition and cinnamon extract in an amount of between 0.01% to 0.5% by volume of the aqueous plaque-reducing composition
and
ii) water in an amount of between 70% and 90% by volume of the aqueous plaque-reducing composition,
wherein the potable aqueous composition is formed by mixing the aqueous plaque-reducing composition with water at a ratio of 1 part aqueous plaque reducing composition to 189 parts water.

3. The method of claim 2, wherein the potable aqueous composition of aqueous plaque-reducing composition and water is administered in a daily dosage of from between 200 ml and 4000 ml.

4. the method of claim 3, wherein the potable aqueous composition of aqueous plaque-reducing composition and water is administered in a daily dosage of at least 400 ml per day.

* * * * *